United States Patent [19]

Wachs et al.

[11] Patent Number: 4,608,359

[45] Date of Patent: Aug. 26, 1986

[54] IRON CARBIDE ON TITANIA SURFACE MODIFIED WITH GROUP VA OXIDES AS FISCHER-TROPSCH CATALYSTS

[75] Inventors: Israel E. Wachs, Bridgewater; Rocco A. Fiato, Scotch Plains; Claudio C. Chersich, Englewood Cliffs, all of N.J.

[73] Assignee: Exxon Research and Engineering Co., Florham Park, N.J.

[21] Appl. No.: 759,669

[22] Filed: Jul. 29, 1985

Related U.S. Application Data

[62] Division of Ser. No. 626,068, Jun. 29, 1984, Pat. No. 4,559,365.

[51] Int. Cl.$^4$ .................. B01J 27/22; B01J 23/20; B01J 21/06; C07C 1/04
[52] U.S. Cl. .................... 502/177; 518/717; 518/720; 518/721
[58] Field of Search ........................ 502/177

[56] References Cited

U.S. PATENT DOCUMENTS

| | | | |
|---|---|---|---|
| 2,539,414 | 1/1951 | Frankenburg | 502/177 |
| 2,543,327 | 2/1951 | McGrath et al. | 502/338 |
| 2,560,345 | 7/1951 | Hemminger | 502/177 |
| 4,154,751 | 5/1979 | McViker et al. | 502/184 |
| 4,192,777 | 3/1980 | McVicker et al. | 502/184 |
| 4,455,395 | 6/1984 | Russemeier | 518/721 |
| 4,559,365 | 12/1985 | Wachs et al. | 518/717 |

FOREIGN PATENT DOCUMENTS

| | | | |
|---|---|---|---|
| 300294 | 11/1928 | United Kingdom | 518/721 |
| 657528 | 9/1951 | United Kingdom | 502/177 |

OTHER PUBLICATIONS

Haensel; "Kaiser Wilhelm Inst. for Kohlenforshung Mulheim" Office of the Publ. Board–Dept. of Commerce–Wash., D.C., 1946, Report No. 284–pp. 4–6.
J. of Catalysis 74, (1982), pp. 199–202, Vannice J.
J. Phys Chem. 84, pp. 3363–3370, Niemantsverdriet et al.
J. of Catalysis 70, (1981), pp. 308–322, Tatarchuk et al.

*Primary Examiner*—P. E. Konopka
*Attorney, Agent, or Firm*—Edward M. Corcoran

[57] ABSTRACT

Catalysts comprising iron carbide on a surface modified titania support wherein said support comprises a surface modifying oxide of tantalum, niobium, vanadium and mixtures thereof supported on said titania wherein at least a portion of said surface modifying oxide is in a non-crystalline form. These catalysts are useful for Fischer-Tropsch hydrocarbon synthesis reactions. Preferably, at least about 25 wt. % of said surface modifying oxide will be in a non-crystalline form.

17 Claims, No Drawings

IRON CARBIDE ON TITANIA SURFACE MODIFIED WITH GROUP VA OXIDES AS FISCHER-TROPSCH CATALYSTS

This is a division of application Ser. No. 626,068, filed June 29, 1984, now U.S. Pat. No. 4,559,365.

BACKGROUND OF THE INVENTION

Field of the Invention

This invention relates to catalyst compositions of matter comprising iron carbide supported on a surface modified titania support. More particularly, this invention relates to Fischer-Tropsch catalyst compositions comprising iron carbide supported on a surface modified titania support, wherein said support comprises a surface modifying oxide of tantalum, vanadium, niobium or mixture thereof supported on the surface of said titania and wherein at least a portion of said surface modifying oxide is in a non-crystalline form.

BACKGROUND OF THE DISCLOSURE

The use of iron-titania mixtures as Fischer-Tropsch catalysts for converting mixtures of CO and $H_2$ to hydrocarbons is well-known to those skilled in the art. For example, U.S. Pat. No. 2,543,327 discloses titania promoted iron oxide for Fischer-Tropsch synthesis wherein the iron oxide is in the form of naturally occurring magnetite and preferably as Alan Wood ore. In this disclosure a typical catalyst is shown as prepared by mixing about 13,600 grams of Alan Wood ore with 98 grams of titania and 216 grams of potassium carbonate used as a promoter. The ratio of hydrogen to carbon monoxide disclosed as being preferably at least 2/1 and the results show that the catalyst has relatively poor activity with a large selectivity towards the production of methane and very little selectivity towards the production of $C_2+$ hydrocarbons. That is, the Fischer-Tropsch product was primarily methane. Similarly, British Pat. No. 1,512,743 also discloses a titania promoted, massive iron type of Fischer-Tropsch catalyst wherein iron oxide is mixed with titanium oxide, zinc oxide and potassium carbonate with the resulting mixture being sintered and then reduced for many hours at 500° C. Although this catalyst has relatively reasonably activity with regard to conversion of the CO and $H_2$ mixture, the product was primarily (i.e., about 73%) olefinic, unsaturated $C_2/C_4$ hydrocarbons and with only about 10% of $C_2/C_4$ saturated hydrocarbons or alkanes being produced. U.S. Pat. Nos. 4,192,777 and 4,154,751 while directed towards the use of potassium promoted Group VA metal cluster catalysts in Fischer-Tropsch synthesis reactions, suggest that iron supported on titania would be useful Fischer-Tropsch catalysts but do not disclose the preparation of same. In their examples, they disclose iron on various supports other than titania with the amount of iron on the support generally being less than about 5percent. U.S. Pat. No. 4,261,865 discloses an iron titanate-alkali metal hydroxide catalyst for preparing alpha-olefins for mixtures of CO and $H_2$. That is, the catalyst is not iron supported on titania along with an alkali methal hydroxide but rather an iron titanate compound.

Another example of a titania-promoted massive iron catalyst for Fischer-Tropsch synthesis may be found in the Volume 17, No. 3–4 React. Kinet. Catal. Lett., pages 373–378, (1971) titled "Hydrocondensation of $CO_2$ (CO) Over Supported Iron Catalysts". This article discloses an iron oxide, titania, alumina, copper oxide catalyst promoted with potassium. Similarly, in European patent application EP 0 071770 A2 Fischer-Tropsch catalysts are disclosed which include iron-titania catalysts wherein the iron to titania ratio can be greater than 1/10. The actual iron-titania catalyst is not an iron supported on titania catalyst but an iron/titania catalyst produced by a coprecipitation technique wherein the active iron catalytic component is distributed throughout a titanium oxide matrix. Thus, the resulting catalyst was not iron supported on titania but rather a bulk phase iron/titania mixture which, when used for Fischer-Tropsch synthesis, produced predominantly olefins. The amount of olefins produced was generally greater than about 80% of the total hydrocarbon product.

With regard to iron/titania catalysts for Fischer-Tropsch wherein the iron is supported on titania, a 1982 article by Vannice, *Titania-Supported Metals as CO Hydrogenation Catalysts*, J. Catalysis, v. 74, p.199–202 (1982), discloses the use of an iron/titania catalyst for Fischer-Tropsch synthesis wherein the amount of iron, calculated as metallic iron, is 5 percent of the iron/titania composite and the catalyst shows extremely little activity for Fischer-Tropsch synthesis. An article by Reymond et al, *Influence of The Support or of an Additive on The Catalytic Activity in The Hydrocondensation of Carbon Monoxide by Iron Catalysts* in "Metal-Support and Metal-Additive Effects in Catalysis", B. Imelik et al (Eds)s, Elsevier, Netherlands, p.337–348 (1982), also discloses the use of iron/titania Fischer-Tropsch catalysts wherein the iron is supported on the titania.

U.S. Pat. No. 4,149,998 to Tauster et al. relates to heterogeneous catalysts consisting of Group VIII metals, including iron, dispersed on oxide carriers selected from the group consisting of Ti, V, Nb, Ta and mixtures thereof and zirconium titanate and $BaTiO_3$. However, there is no suggestion in this patent that the catalytic metal be dispersed on a surface modified titania.

SUMMARY OF THE INVENTION

It has now been discovered that catalysts comprising iron carbide supported on a surface modified titania support wherein said support comprises a surface modifying oxide of tantalum, niobium, vanadium and mixture thereof supported on the surface of said titania and wherein at least a portion of said surface modifying oxide is in a non-crystalline form are useful catalysts for Fischer-Tropsch hydrocarbon synthesis. Moreover, Fischer-Tropsch reactions conducted with these catalysts have been found to result in increased olefin and decreased methane make compared to Fischer-Tropsch catalysts comprising iron supported on titania wherein the surface of the titania has not been modified with a Group VA modifying oxide. Further, the catalysts of this invention produce a greater amount of heavier products and exhibit superior catalyst maintenance than similar catalysts on titania whose surface has not been modified with a Group VA oxide.

In a preferred embodiment at least about 25 wt. % of the surface modifying oxide of tantalum, niobium, vanadium or mixture thereof present on the titania surface will be in a non-crystalline form. In a particularly preferred embodiment, the catalyst will be pretreated with CO at elevated temperature prior to use.

The catalyst will contain at least about 2 milligrams of iron, calculated as $Fe_2O_3$, per square meter of support surface. In general, the amount of supported iron carbide, calculated as iron, will range from about 2 to 20 wt. % of the total catalyst composition. In a preferred embodiment, the amount of supported iron carbide, calculated as iron, will range from about 4 to 10 wt. % of the total catalyst composition.

DETAILED DESCRIPTION

The term surface modified titania as used herein refers to titania whose surface has been modified by an oxide of niobium, vanadium, tantalum and mixture thereof in an amount such that the modified support exhibits properties different from titania whose surface has not been modified and also different from bulk niobia, tantala, vanadia and mixture thereof. Concomitantly, the final catalyst composition will exhibit properties different from iron carbide supported on unmodified titania or on bulk niobia, tantala, vanadia and mixture thereof.

Thus, the catalyst support useful for preparing the catalysts of this invention comprise titania whose surface has been modified with an oxide of a Group VA metal (vanadium, niobium, tantalum and mixture thereof). That is, the surface of the titania has been modified by an oxide of vanadium, niobium, tantalum and mixture thereof in an amount such that the catalyst exhibits properties different from titania whose surface has not been modified and different from bulk oxides of vanadium, niobium, tantalum and mixture thereof. Those skilled in the art know that the oxides of niobium, tantalum, vanadium and mixtures thereof are crystalline in their bulk form. Thus, at least a portion of and preferably at least about 25 wt. % of the Group VA metal oxide will be in a non-crystalline form. This will be accomplished if the metal oxide loading on the titania broadly ranges between about 0.5 to 25 wt. % of the total catalyst weight.

In the catalyst of this invention the iron carbide is supported on the surface modified titania. Consequently, the catalysts of this invention are prepared by a two-step sequential process wherein the surface modified titania support is prepared first, followed by depositing the iron carbide or iron carbide precursor on the support. Thus, in the first step an oxide or precursor thereof of a metal selected from the group consisting of niobium, tantalum, vanadium and mixture thereof is deposited on the titania to form either the surface modified support or, in the case of one or more precursors, a support precursor. The support precursor will then be calcined to oxidize the oxide precursor and form a support comprising titania whose surface has been modified by an oxide of a metal selected from the group consisting of niobium, tantalum, vanadium and mixture thereof wherein at least a portion of said surface modifying oxide is in a non-crystalline form.

The catalyst support precursors of this invention may be prepared by techniques well-known in the art, such as incipient wetness, impregnation, etc., the choice being left to the practitioner. When using the impregnation technique, the impregnating solution is contacted with the titania for a time sufficient to deposit the oxide precursor material onto the titania either by selective adsorption or alternatively, the excess solvent may be evaporated during drying leaving behind the precursor salt. If an impregnation or incipient wetness technique is used to prepare a support precursor of this invention, the transition metal oxide salt solution used may be aqueous or organic, the only requirement being that an adequate amount of precursor compound for the selected Group VA transition metal oxide or oxides be soluble in the solvent used in preparing this solution.

The support precursor composite will then normally be dried at temperatures ranging from about 50°–300° C. to remove the excess solvent and, if necessary, decompose the salt if it is an organic salt to form a catalyst precursor. The support precursor composite is then converted into the surface modified titania support by calcining at temperatures of from about 150° to 800° C. and preferably 300°–700° C. in a suitable oxidizing atmosphere such as air, oxygen, etc. The time required to calcine the composite will, of course, depend on the temperature and in general will range from about 0.5–7 hours. Reducing atmospheres may also be used to decompose the transition metal oxide precursors, but the resulting composite will then require subsequent calcination to convert the reduced metal component to the oxide form.

The supports of this invention will generally have metal oxide loadings of from about 0.5 to 25 wt. % metal oxide on the titania based on the total support composition, preferably from about 1 to 15 wt. %, more preferably from about 2–10 wt. % based on the total support composition.

It is important to this invention that the iron carbide is supported on and not merely mixed with the surface modified titania support.

The catalyst will be prepared by depositing a suitable iron precursor component onto the surface modified titania support from a precursor solution using any of the well-known techniques such as incipient wetness, multiple impregnation, pore-filling etc., the choice being left to the convenience of the practitioner. As has heretofore been stated, it is important for the iron precursor to be deposited onto the support as opposed to other methods for catalyst preparation such as coprecipitation or physical mixtures. After impregnation, the impregnate is dried to remove excess solvent and/or water therefrom. The dry impregnate can then be converted to a catalyst of this invention employing a number of different methods. In one method, the impregnate will be converted directly to a catalyst of this invention by contacting same with a CO containing reducing gas, preferably a reducing gas containing a mixture of CO and $H_2$. Thus, it will be appreciated to those skilled in the art that the catalyst of this invention can be formed from the impregnate in-situ in a Fischer-Tropsch hydrocarbon synthesis reactor. However, it is preferred to employ a sequential treatment of first contacting the dry impregnate with an $H_2$ containing reducing gas that does not contain CO to reduce the impregnate, followed by contacting the reduced impregnate with CO or a CO containing gas such as a mixture of CO and $H_2$ to form the catalyst of this invention. As a practical matter, it may be commercially advantageous to form the catalyst of this invention by subjecting the impregnate to calcining to convert the supported iron precursor component to iron oxide, followed by subsequent reduction and formation of the catalyst of this invention.

Promoter metals such as potassium or other alkali metals may be added via impregnation, etc. before the composite is contacted with a reducing atmosphere and/or CO containing gas to form the catalyst of this invention. In general, the amount of promoter metal present will range from about 0.5 to 5 wt. % based on the amount of iron (calculated as $Fe_2O_3$) supported on the titania.

If one desires to obtain a catalyst of this invention via a supported iron oxide route, then the dry impregnate will be calcined in air or other suitable oxidizing atmosphere at a temperature of from about 120° to 300° C. for a time sufficient to convert the supported iron precursor component to iron oxide. After the iron/surface modified titania impregnate has been calcined to convert the supported iron precursor compound to iron oxide, the iron oxide/titania composite with or without one or more promoter metals, is reduced in a hydrogen-containing, net-reducing atmosphere at a temperature broadly ranging from about 300°–500° C. for a time sufficient to convert the iron oxide to metallic iron. It has been found that if one tries to reduce the iron oxide/titania composite at a temperature below about 300° C., (i.e., 250°C), the catalyst of this invention will not subsequently be formed.

Irrespective of the route one employs to form a catalyst of this invention, whether by reduction followed by contacting with CO, direct formation of the catalyst or through the supported iron oxide route, it is important not to contact the composite with a reducing gas at temperatures above about 500° C.

Reduction temperatures exceeding about 500° C. will produce a catalyst which exhibits relatively low CO hydrogenation activity with less than 50% of the $C_{2+}$ hydrocarbons being alkanes. Further, even at a 500° C. reduction temperature a less effective catalyst will be produced if the reduction occurs for too long a time, i.e., about ten hours or more. Thus, it will be appreciated that the temperature range for reducing the composite to form a catalyst cannot be critically quantified with any degree of precision inasmuch as there exists a time-temperature continuum for proper reduction.

In a preferred embodiment of this invention, the catalyst composite will first be reduced, followed by contacting with CO at temperatures ranging from about 200° to 500° C. and preferably 200° to 400° C. for a time sufficient to form a catalyst comprising iron carbide supported on the surface modified titania. It has been found that a CO treatment following hydrogen reduction dramatically improves the activity of the catalyst for CO conversion with only slight changes in product selectivity. Iron carbide on the surface modified titania support will also be achieved by treating the calcined iron/support composite with a mixture of CO and $H_2$, but it is preferred to use the sequential treatment comprising hydrogen reduction followed by CO treatment. Further, when using this sequential treatment to produce a catalyst of this invention, it is preferred that the temperature used for the CO treatment be lower than that used for the hydrogen reduction. Thus, in general the CO treatment will occur at a temperature of about 100° to 200° C. lower than the temperature used for the hydrogen reduction.

It has also been discovered that, if a catalyst of this invention has been prepared by hydrogen reduction and then contacted in-situ, in a reactor, with a feedstream comprising a mixture of CO and $H_2$ to form a catalyst of this invention, the activity of the so formed catalyst will be substantially increased by reducing or eliminating the hydrogen content of the feedstream, raising the temperature in the reactor an additional 50° to 150° C. for a short period of time (i.e., 3–5 hours), followed by reestablishing the original reaction conditions.

Predominantly $C_{2+}$ alkane hydrocarbons are produced from mixtures of CO and $H_2$ by contacting said mixtures with the catalyst of this invention at temperatures ranging from about 200° to 350° C. and preferably from about 250°–320° C. The reaction pressure will generally range from about 100–500 psig and more preferably from about 150–300psig, although pressures outside this range may be used if desired. However, if one goes too low in pressure (i.e., <50 psig), catalyst activity will be greatly reduced and methane production will predominate. Upper pressure limits will generally be dictated by economic considerations. The $H_2/CO$ mole ratio in the reaction zone will generally range from about ½ to 3/1, preferably from about ½ to 2/1 and still more preferably from about ½ to 1/1.

The invention will be more readily understood by reference to the following examples.

Catalyst Support Preparation

Degussa P-25, a mixture of anatase and rutile titania, was used as the titania support. Both of the catalyst supports were prepared in a glove box in a nitrogen atmosphere to prevent decomposition of the transition metal oxide precursors. In all cases 10 grams of the P-25 titania powder were slurried in 100 cc of ethanol to which was added the transition metal oxide precursor, with the resulting mixture stirred overnight, under flowing nitrogen, to evaporate the ethanol. Each dry mixture was then taken out of the glove box and 3 cc of water added. The resulting mixture was stirred overnight in air, then the dry powder placed in a quartz boat and slowly heated in a 1/1 flowing mixture of $O_2$ in He up to 400° C. At 400° C. the He flow was cut off and the powdered, catalyst support precursor then heated from 400° to 575° C. in 100% $O_2$. Each sample of catalyst precursor was held at 575° C. in the $O_2$ for two hours to calcine the precursor into a surface modified titania support of this invention.

The transition metal oxide precursors were obtained from Alfa, Inc. and were $Nb(C_2H_5O)_5$ and $VO(C_2H_5O)_3$. The amounts of niobia and vanadia precursors added to each slurry of 10 g P-25 in 100 cc of ethanol were 2.5 and 0.46 grams, respectively. The resulting catalysts contained 10 wt. % niobia on titania and 2wt. % vanadia on titania. The niobia and vanadia contents of the catalysts were expressed as niobium pentoxide and vanadium pentoxide.

Example 1

A 5–8 cc sample of catalyst, containing 4 wt. % Fe as elemental iron on the support, was loaded into a ⅜ inch O.D. 316 stainless steel tubular reactor. The system was then flushed with nitrogen at atmospheric pressure and then flushed with 90% $H_2$/10% $N_2$ at atmospheric pressure. The reactor was then heated to 500° C. in flowing 90% $H_2$/10% $N_2$ (100 cc/min) and maintained at these conditions for 5 hrs. After this, the reactor was cooled to the desired reaction temperature, 290°–315° C., and the pressure increased to 300 psig. The reducing gas was then replaced with 1/1 $H_2$/CO at a flow rate (standard hourly space velocity) of 500 V/V/hr. The exit gas from the reactor was fed into a gas chromatograph for on-line analysis of $C_1$–$C_{15}$ hydrocarbons, CO, $CO_2$ and $N_2$.

The results of Runs A–D are presented in the Table 1. The runs can be compared either at conditions for nearly equal conversion, run A vs. Run C and Run B vs. Run D, or at identical conditions, Run A vs. Run D. In all cases the vanadium containing system is found to generate lower levels of methane than the standard catalyst. Comparison of these catalysts at identical conditions, Run A vs. Run D at 350° C., also indicates that the vanadium containing system is more active. The modified $TiO_2$ catalyst of the present invention is clearly superior to the unmodified analog for production of desired α-olefin products while minimizing the formation of unwanted methane.

TABLE 1

| Run | 4 wt. % Iron on Titania | | 4 wt. % Iron on Titania Surface Modified With An Oxide of Vanadium | |
|---|---|---|---|---|
| | A | B | C | D |
| Temp. °C. | 305 | 315 | 290 | 305 |
| % CO Conversion | 47 | 60 | 49 | 70 |
| Wt. % Selectivity ($CO_2$ Free) | | | | |
| $CH_4$ | 21.0 | 24.4 | 16.1 | 17.8 |
| $C_2^=$ | 0.4 | 0.6 | 2.7 | 2.8 |
| $C_2°$ | 16.1 | 16.2 | 20.2 | 16.8 |
| $C_3^=$ | 11.7 | 9.7 | 16.6 | 18.6 |
| $C_3°$ | 13.7 | 12.7 | 14.4 | 16.5 |
| $C_4^=$ | 2.5 | 3.0 | 1.9 | 2.0 |
| $C_4°$ | 7.1 | 7.4 | 8.1 | 10.9 |
| $C_5+$ | 27.5 | 26.0 | 20.0 | 14.6 |

Conditions: 1:1 $H_2$:CO, 500 v/v/hr, 300 psig, pretreatment with $H_2$ at 500° C. for 5 hr. $C_5+$ determined by nitrogen internal standard method.

The activity and carbon number distributions for the unmodified $Fe/TiO_2$ and the V and Nb surface modified $Fe/TiO_2$ catalysts during Fischer-Tropsch synthesis are presented in Table 2. The addition of V and Nb affected the activity and selectivity of the $Fe/TiO_2$ catalysts. The incorporation of V and Nb to the $TiO_2$ surface increased and decreased the conversion of CO, respectively. The stability of the modified catalysts was superior to that of the unmodified $Fe/TiO_2$ catalyst (less coking). The V and Nb modified $Fe/TiO_2$ catalysts substantially decreased the $CH_4$ yield and increased the $C_5+$ yield. Whereas $Fe/TiO_2$ yields substantial amounts of paraffins (70–90%) paraffins in hydrocarbon) the V and Nb modified $Fe/TiO_2$ catalysts produced substantial amounts of olefins and low amounts of paraffins. In addition, XRD analysis of the spent V and Nb modified $Fe/TiO_2$ catalysts did not show the presence of $FeTiO_3$ in the catalysts. Thus, the addition of V and Nb to the surface of the $TiO_2$ altered the $Fe-TiO_2$ interaction and the nature of the products obtained from such a catalyst during Fischer-Tropsch synthesis.

TABLE 2

| | 4% $Fe/TiO_2$ | 4% $Fe(TiO_2$ + V oxide) | 4% $Fe(TiO_2$ + Nb oxide) |
|---|---|---|---|
| % CO Conversion | 27.0 | 34.3 | 20.1 |
| $C_1$ | 21.0 | 13.0 | 14.6 |
| $C_2$ | 17.0 | 21.5 | 15.0 |
| $C_3$ | 29.0 | 12.0 | 11.9 |
| $C_4$ | 9.0 | 8.0 | 6.0 |
| $C_5+$ | 24.0 | 45.5 | 52.5 |

CONDITIONS: 270° C., 300 psia, 500–600 V/V/M, $H_2$:CO = 1

What is claimed is:

1. A catalyst comprising iron carbide supported on a surface modified titania support wherein said support comprises an oxide of a metal selected from the group consisting of niobium, vanadium, tantalum or mixture thereof supported on said titania wherein at least a portion of said supported oxide of niobium, vanadium, tantalum or mixture thereof is in a non-crystalline form, wherein the amount of said supported oxide ranges from about 0.5 to 25 weight percent metal oxide on the titania support based on the total support composition and wherein the catalyst contains at least about 2 milligrams of iron, calculated as $Fe_2O_3$, per square meter of support surface.

2. The catalyst of claim 1 containing one or more alkali metal promoters.

3. The catalyst of claim 2 wherein the amount of said iron carbide, calculated as iron, ranges from about 2 to 20 wt. % of the total catalyst composition.

4. The catalyst of either of claims 1, 2 or 3 wherein at least about 25 wt. % of said supported oxide is non-crystalline.

5. The catalyst of claim 4 wherein the amount of supported iron carbide, calculated as iron, ranges from about 4 to 10 wt. % of the total catalyst composition.

6. A process for producing a catalyst comprising iron carbide supported on a surface modified titania support wherein said support comprises an oxide of a metal selected from the group consisting of niobium, vanadium, tantalum or mixture thereof supported on titania wherein at least a portion of said supported oxide is in a non-crystalline form and wherein the amount of said oxide supported on said titania support ranges from about 0.5 to 25 wt. % metal oxide based on the total support composition, said process comprising the steps of:

(a) depositing iron on the surface modified titania support from a solution of iron precursor compound in an amount such that the final catalyst will contain supported iron in an amount of at least about 2 milligrams of iron, calculated as $Fe_2O_3$, per square meter of support surface;

(b) calcining the iron precursor supported on titania produced in step (a) at a temperature of from about 120° to 500° C. for a time sufficient to decompose said iron precursor material and convert at least a portion of said supported iron to $Fe_2O_3$; and (c) contacting said calcined composite formed in step (b) with hydrogen at a temperature of from between about 150°–800° C. for a time sufficient to convert at least a portion thereof to a reduced composite; and (d) contacting said reduced composite formed in (c) with CO at an elevated temperature of at least about 200° C. for a time sufficient to form said catalyst.

7. The process of claim 6 wherein said reduced composite is contacted with CO at a temperature broadly ranging between about 200° to 500° C. prior to use.

8. The process of claim 6 wherein said catalyst contains one or more alkali metal promoters.

9. The process of claim 7 wherein said catalyst contains one or more alkali metal promoters.

10. The process of either of claims 6, 7, 8 or 9 wherein the amount of iron carbide present in said catalyst, calculated as iron, ranges from about 2 to 20 wt. % of the total catalyst composition.

11. The process of claim 10 wherein at least about 25 wt. % of said supported oxide of niobium, tantalum, vanadium or mixture thereof is non-crystalline.

12. The process of claim 11 wherein the amount of supported iron carbide, calculated as iron, ranges from about 4 to 10 wt. % of the total catalyst composition.

13. As a composition of matter, a composite produced by the steps of:

(a) depositing a precursor material of an oxide of a metal selected from the group consisting of niobium, tantalum, vanadium or mixture thereof on the surface of titania to form a precursor/titania composite;

(b) calcining the composite formed in step (a) above to convert the precursor to the oxide to form the surface modified titania support wherein said so-formed oxide is present on the surface of the titania in an amount of from about 0.5 to 25 wt. % based on the support composition;

(c) depositing iron on the surface modified titania support from a solution of iron precursor compound in an amount such that the final catalyst will contain supported iron in an amount of at least about 2 milligrams of iron, calculated as $Fe_2O_3$, per square meter of titania support surface;

(e) calcining the iron precursor supported on titania produced in step (a) at a temperature of from about 120° to 500° C. for a time sufficient to decompose said iron precursor material and convert at least a portion of said supported iron to $Fe_2O_3$;

(f) contacting said calcined composite formed in step (e) with hydrogen at a temperature of from between about 150°–800° C. for a time sufficient to convert at least a portion thereof to a reduced composite; and (g) contacting said reduced composite formed in (f) with CO at an elevated temperature of at least about 200° C. for a time sufficient to form said catalyst.

14. The composition of matter produced by the process of claim 13 wherein said reduced composite is contacted with CO at a temperature broadly ranging between about 200° to 500° C. prior to use.

15. The composition of matter produced by the process of claim 14 wherein the amount of supported iron carbide, calculated as iron, ranges from about 2 to 20 wt. % of the total catalyst composition.

16. The composition of matter produced by the process of claim 15 wherein at least 25 wt. % of said supported oxide of niobium, tantalulm, vanadium or mixtures thereof is non-crystalline.

17. The composition of matter produced by the process of either of claims 12, 13, 14, 15 or 16 wherein said catalyst contains one or more alkali metal promoters.

* * * * *